(12) United States Patent
Tran et al.

(10) Patent No.: US 10,420,894 B2
(45) Date of Patent: Sep. 24, 2019

(54) DOSE DIVIDER SYRINGE

(71) Applicant: TELEFLEX MEDICAL INCORPORATED, Morrisville, NC (US)

(72) Inventors: Huy Tran, Riverton, UT (US); Perry Croll, Sandy, UT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 108 days.

(21) Appl. No.: 15/052,665

(22) Filed: Feb. 24, 2016

(65) Prior Publication Data

US 2016/0243313 A1   Aug. 25, 2016

Related U.S. Application Data

(60) Provisional application No. 62/119,912, filed on Feb. 24, 2015.

(51) Int. Cl.
*A61M 5/315* (2006.01)
*A61M 5/28* (2006.01)
(Continued)

(52) U.S. Cl.
CPC ... *A61M 5/31548* (2013.01); *A61B 17/00491* (2013.01); *A61M 5/283* (2013.01);
(Continued)

(58) Field of Classification Search
CPC ............ A61M 5/31548; A61M 11/007; A61M 5/31595; A61M 2005/3118; A61M 5/343;
(Continued)

(56) References Cited

U.S. PATENT DOCUMENTS 2,554,451 A * 5/1951 Barry .................. A61M 5/2429
604/203
3,770,026 A * 11/1973 Isenberg ........... A61M 5/31525
141/2
(Continued)

FOREIGN PATENT DOCUMENTS

EP       2832452 A1   2/2015
GB       2163490 A    2/1986
(Continued)

*Primary Examiner* — Laura A Bouchelle
*Assistant Examiner* — Dung T Ulsh
(74) *Attorney, Agent, or Firm* — Baker & Hostetler LLP (57) ABSTRACT

A syringe includes a barrel having an internal surface defining an internal bore therein; a plunger having a distal end disposed within the internal bore of the barrel, and a proximal end disposed outside the internal bore of the barrel, the proximal end of the plunger being opposite the distal end of the plunger along a longitudinal direction; and a dose divider. The dose divider includes a divider flange extending at least partly in a radial direction, the radial direction being perpendicular to the longitudinal direction, the divider flange having a distal surface that faces the barrel, the distal surface of the divider flange bearing on the proximal end of the plunger, and a concave shell extending away from the distal surface of the divider flange along the longitudinal direction.

12 Claims, 9 Drawing Sheets

(51) Int. Cl.
  *A61B 17/00* (2006.01)
  *A61M 15/08* (2006.01)
  *A61M 11/00* (2006.01)
  *A61M 5/31* (2006.01)
  *A61B 90/00* (2016.01)

(52) U.S. Cl.
  CPC ...... *A61M 5/31595* (2013.01); *A61M 11/007* (2014.02); *A61M 15/08* (2013.01); *A61B 2017/00907* (2013.01); *A61B 2090/034* (2016.02); *A61B 2090/0811* (2016.02); *A61M 5/288* (2013.01); *A61M 5/3137* (2013.01); *A61M 5/31501* (2013.01); *A61M 2205/582* (2013.01); *A61M 2205/586* (2013.01)

(58) Field of Classification Search
  CPC .............. A61M 5/349; A61M 5/31501; A61M 5/31525; A61M 5/31565
  See application file for complete search history.

(56) References Cited

U.S. PATENT DOCUMENTS

| | | | | |
|---|---|---|---|---|
| 4,073,321 | A * | 2/1978 | Moskowitz | A61M 5/1782 141/27 |
| 4,424,057 | A | 1/1984 | House | |
| 4,563,178 | A * | 1/1986 | Santeramo | A61M 5/1782 141/27 |
| 4,946,441 | A * | 8/1990 | Laderoute | A61J 1/1406 604/110 |
| 5,104,380 | A | 4/1992 | Holman et al. | |
| 5,263,934 | A | 11/1993 | Van de Haak | |
| 5,300,041 | A | 4/1994 | Haber et al. | |
| 5,601,077 | A * | 2/1997 | Imbert | A61M 11/00 128/200.14 |
| 5,662,098 | A * | 9/1997 | Yoshida | B05B 1/3436 128/200.22 |
| 5,951,526 | A * | 9/1999 | Korisch | A61M 5/3129 604/208 |
| 6,382,465 | B1 | 5/2002 | Greiner-Perth | |
| 7,611,495 | B1 * | 11/2009 | Gianturco | A61M 5/31501 604/207 |
| 2006/0111676 | A1 | 5/2006 | Millerd | |
| 2010/0065062 | A1 * | 3/2010 | Rajan | A61M 16/0488 128/207.14 |
| 2014/0031763 | A1 * | 1/2014 | Soma | A61M 5/31505 604/208 |
| 2014/0180217 | A1 * | 6/2014 | Kuczek | A61M 5/31501 604/208 |
| 2014/0180245 | A1 * | 6/2014 | Wong | A61M 5/315 604/506 |
| 2014/0303565 | A1 * | 10/2014 | Kubo | A61M 15/08 604/208 |
| 2015/0157801 | A1 * | 6/2015 | Tran | A61M 5/31591 604/208 |
| 2016/0022920 | A1 * | 1/2016 | Reeves | A61M 5/31536 604/506 |
| 2016/0243313 | A1 * | 8/2016 | Tran | A61M 5/283 |
| 2016/0325080 | A1 * | 11/2016 | Glynn | A61M 11/00 |

FOREIGN PATENT DOCUMENTS

| | | |
|---|---|---|
| JP | 61-30699 U | 2/1986 |
| JP | 11-151301 | 6/1999 |
| JP | 2001-113210 A | 4/2001 |
| WO | WO-03004080 A1 * | 1/2003 .......... A61M 5/3146 |
| WO | 2013/145789 A1 | 10/2013 |
| WO | 2014/147594 A1 | 9/2014 |

* cited by examiner

DOSE DIVIDER SYRINGE

CROSS-REFERENCE TO RELATED APPLICATIONS

This application claims priority to U.S. Provisional Patent Application No. 62/119,912, filed Feb. 24, 2015, the disclosure of which is hereby incorporated by reference in its entirety.

TECHNICAL FIELD

This patent disclosure relates generally to syringes and, more particularly, to syringes that provide tactile feedback of a quantity of material delivered by operation thereof.

BACKGROUND

Syringes are known for storing and transporting substances with fluid properties such as gases, liquids, pastes, slurries, or any other material that tends to flow in response to applied shear stress. A syringe may include a barrel defining a bore in communication with a port, and a plunger disposed within the barrel. Translation of the plunger away from the port may draw material into the barrel through the port. Alternatively, translation of the plunger toward the bore may expel material from the barrel out of the port.

A syringe barrel may be formed from a transparent or translucent material, such that a position of the plunger within the bore is visible through the barrel. Further, the syringe barrel may include indicia disposed thereon, such that longitudinal alignment of the plunger relative to the indicia may visually indicate a volume of material stored within the syringe.

U.S. Pat. No. 5,104,380 (hereinafter, "the '380 patent") purports to describe a dose metering device for use in conjunction with a syringe and to syringes incorporating such devices. The syringe from the '380 patent includes a body and a dose-setting device mounted on the body and capable of being moved to a selected set position, a latch arranged to retain the setting device in the set position, and means arranged to release the latch to cause the set dose to be expelled. Further according to the '380 patent, movement of the dose-setting device to the selected set position is accompanied by straining of a spring, which, when the latch is released, provides the force for expelling the set dose. However, the latch and spring mechanism of the dose-setting device in the '380 patent may be complex to assemble, expensive to manufacture, require detailed operating instructions for users, or combinations thereof.

U.S. Pat. No. 5,300,041 (hereinafter, "the '041 patent") purports to describe a dose setting and repeating syringe device which allows repetitive injection of a pre-programmed dose amount from a volume of insulin or other pharmaceutical contained within the syringe. A syringe according to the '041 patent includes a mechanical dose programming assembly coupled to a proximal end of a hollow barrel and including a dose ring and a dose plunger slidably mounted onto the dose ring and coupled to a ratchet stem. The dose ring of the '041 patent is threadably mounted onto the proximal end of the hollow barrel and provides adjustable programming of sliding travel of the dose plunger relative to the hollow barrel. However, the mechanical dose programming assembly of the '041 patent may be complex to assemble, expensive to manufacture, require detailed operating instructions for users, or combinations thereof.

Accordingly, there is a need for an improved syringe to address the aforementioned problems and/or other problems in the art.

SUMMARY

According to an aspect of the disclosure, a dose divider for a syringe comprises a flange extending at least partly in a radial direction, and a concave shell extending away from the flange along a longitudinal direction, the longitudinal direction being perpendicular to the radial direction, a proximal end of the concave shell being disposed on the flange, and a distal end of the concave shell being opposite the proximal end of the concave shell along the longitudinal direction. The concave shell extends in a circumferential direction about an axis from a first circumferential edge to a second circumferential edge, the axis being aligned with the longitudinal direction, and the first circumferential edge is separated from the second circumferential edge by a gap distance. In another aspect, the gap distance spans a first distance at the proximal end of the concave shell, the gap spans a second distance at the distal end of the concave shell, and the second distance is greater than the first distance. In another aspect, the concave shell subtends an angle in the circumferential direction about the axis from the first circumferential edge to the second circumferential edge that is greater than 180 degrees. In another aspect, the angle in the circumferential direction is less than 270 degrees, or, less than 230 degrees.

According to an aspect of the disclosure, a syringe comprises a barrel having an internal surface defining an internal bore therein; a plunger having a distal end disposed within the internal bore of the barrel, and a proximal end disposed outside the internal bore of the barrel, the proximal end of the plunger being opposite the distal end of the plunger along a longitudinal direction; and a dose divider comprising a flange extending at least partly in a radial direction, and a concave shell extending away from the flange along a longitudinal direction, the longitudinal direction being perpendicular to the radial direction, a proximal end of the concave shell being disposed on the flange, and a distal end of the concave shell being opposite the proximal end of the concave shell along the longitudinal direction. The concave shell extends in a circumferential direction about an axis from a first circumferential edge to a second circumferential edge, the axis being aligned with the longitudinal direction, and the first circumferential edge is separated from the second circumferential edge by a gap distance. In another aspect, the gap distance spans a first distance at the proximal end of the concave shell, the gap spans a second distance at the distal end of the concave shell, and the second distance is greater than the first distance. In another aspect, the concave shell subtends an angle in the circumferential direction about the axis from the first circumferential edge to the second circumferential edge that is greater than 180 degrees. In another aspect, the angle in the circumferential direction is less than 270 degrees, or, less than 230 degrees. In an aspect, the dose divider is removably coupled to the plunger and configured to bear on the barrel in response to translation of the plunger relative to the barrel along the longitudinal direction, the dose divider including a distal surface that faces the barrel, the distal surface of the divider flange bearing on the proximal end of the plunger, and the concave shell of the dose divider extending away from the distal surface of the divider flange along the longitudinal direction, the length of the dose divider in said longitudinal direction being shorter than the length of the plunger.

According to another aspect of the disclosure, a method for delivering a material using a syringe, comprises installing a dose divider on a proximal end of a plunger, such that the concave shell of the dose divider at least partly surrounds the plunger about a longitudinal axis of the plunger; expelling a first portion of the material from the syringe by translating the plunger from a first position to a second position relative to a barrel along the longitudinal axis; bearing a distal end of the dose divider against the barrel; removing the dose divider from the plunger; and expelling a second portion of the material from the syringe by translating the plunger from the second position to a third position relative to the barrel along the longitudinal axis. In an aspect, the dose divider comprises a flange extending at least partly in a radial direction, and a concave shell extending away from the flange along a longitudinal direction, the longitudinal direction being perpendicular to the radial direction, a proximal end of the concave shell being disposed on the flange, and a distal end of the concave shell being opposite the proximal end of the concave shell along the longitudinal direction. The concave shell extends in a circumferential direction about an axis from a first circumferential edge to a second circumferential edge, the axis being aligned with the longitudinal direction, and the first circumferential edge is separated from the second circumferential edge by a gap distance. In another aspect, the gap distance spans a first distance at the proximal end of the concave shell, the gap spans a second distance at the distal end of the concave shell, and the second distance is greater than the first distance. In another aspect, the concave shell subtends an angle in the circumferential direction about the axis from the first circumferential edge to the second circumferential edge that is greater than 180 degrees. In another aspect, the angle in the circumferential direction is less than 270 degrees, or, less than 230 degrees.

DETAILED DESCRIPTION

Aspects of the disclosure will now be described with reference to the drawing figures, in which like reference numerals refer to like parts throughout, unless specified otherwise.

Figure 1A:
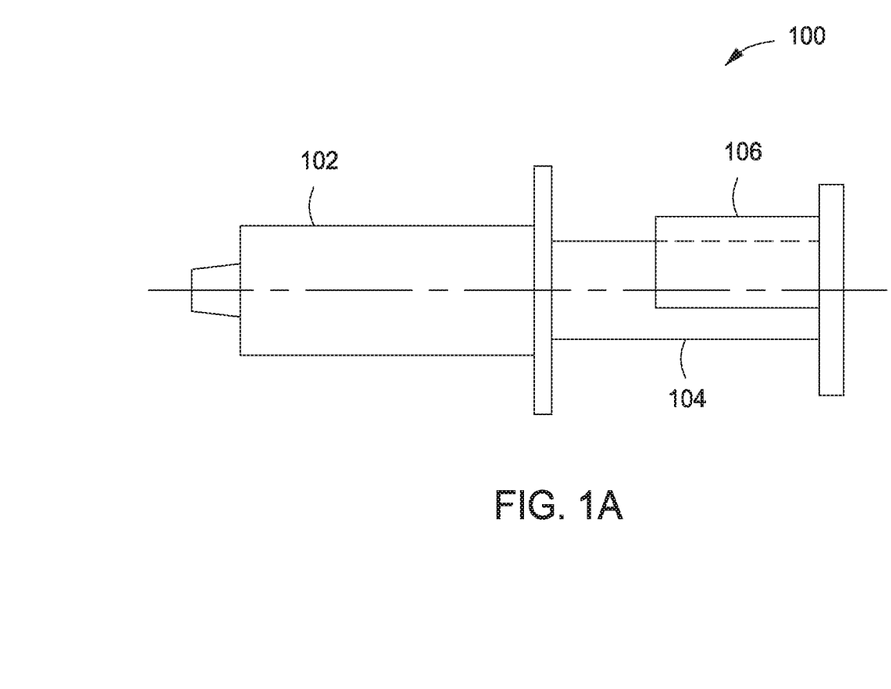
FIG. 1A shows a front view of a syringe, according to an aspect of the disclosure.
Figure 1B:
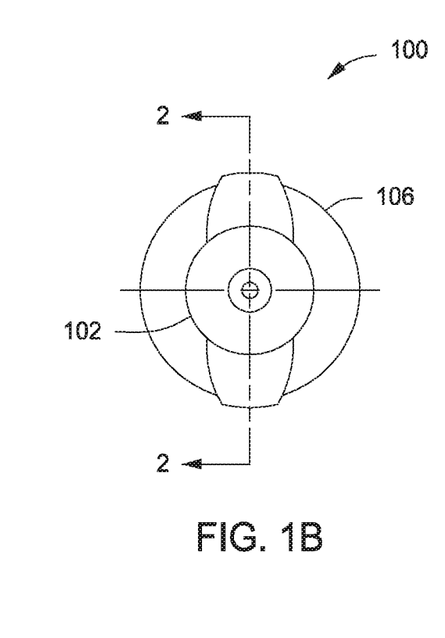
FIG. 1B shows a left side view of a syringe, according to an aspect of the disclosure.

Referring to FIGS. 1A and 1B (collectively "FIG. 1"), it will be appreciated that FIG. 1A shows a front view of a syringe 100, according to an aspect of the disclosure; and FIG. 1B shows a left side view of a syringe 100, according to an aspect of the disclosure. The syringe 100 includes a barrel 102, a plunger 104, and a dose divider 106. The plunger 104 is disposed at least partly within the barrel 102, and the plunger 104 is configured for sliding engagement within the barrel 102. The dose divider 106 is removably attached to the plunger 104.

Figure 2:
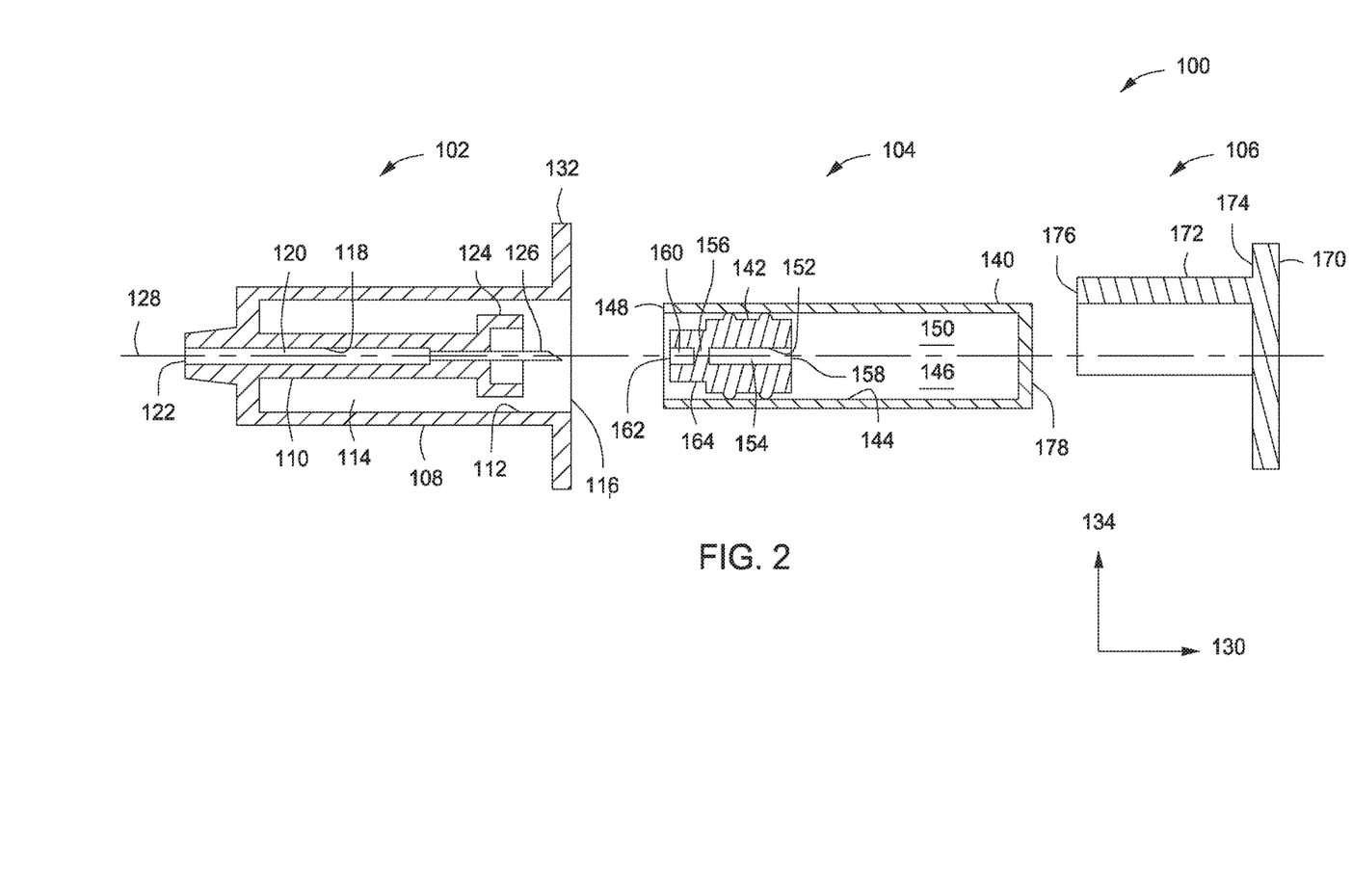
FIG. 2 is an exploded front cross sectional view of the syringe along the section line 2-2, according to an aspect of the disclosure.

FIG. 2 is an exploded front cross sectional view of the syringe 100 along the section line 2-2, according to an aspect of the disclosure. The barrel 102 includes an outer wall 108 and an inner stem 110 disposed within the outer wall 108. The outer wall 108 includes an internal surface 112 that defines a barrel cavity 114 therein, and defines a proximal aperture 116 of the outer wall 108. The inner stem 110 includes an internal surface 118 that defines a stem cavity 120 therein, and that defines a distal aperture 122 of the inner stem 110. The distal aperture 122 may be fluidly coupled to an outlet cannula or needle, a fluid atomizer, or any other syringe outlet structure known in the art.

The inner stem also includes a stem connector 124 and a cannula 126. The cannula 126 projects through the stem connector 124, and is in fluid communication with the distal aperture 122 via the stem cavity 120. The stem connector 124 may be a threaded connector, a tapered connector, an interference connector, a Luer-type connector, or any other connector known in the art.

According to an aspect of the disclosure, the cannula 126 and the distal aperture 122 are each aligned on a longitudinal axis 128 of the syringe 100, such that the cannula 126 projects away from the distal aperture 122 along a longitudinal direction 130. According to another aspect of the disclosure, the cannula 126 and the stem connector 124 are each aligned on the longitudinal axis 128. However, it will be appreciated that the cannula 126 need not be coaxial with either the distal aperture 122 or the stem connector 124.

The barrel 102 further includes a flange 132 that projects away from the outer wall 108 at least partly in a radial direction 134, where the radial direction 134 is perpendicular to the longitudinal direction 130. According to an aspect of the disclosure, the flange 132 projects away from the outer wall 108 in the radial direction 134.

The plunger 104 includes a vial 140 and a piston 142. The vial 140 includes an internal surface 144 that defines a vial cavity 146, and that defines a distal aperture 148 of the plunger 104. The piston 142 is disposed within the vial cavity 146 in sliding and sealing engagement with the internal surface 144 of the vial 140. Accordingly, the internal surface 144 and the piston 142 may define, at least in part, an internal volume or fluid chamber 150 having a variable volume depending upon a location of the piston 142 within the vial 140 along the longitudinal direction 130.

The piston 142 includes an internal surface 152 that may define a proximal conduit 154 extending from a septum 156 to a proximal aperture 158 of the piston 142, where the proximal aperture 158 is in fluid communication with the fluid chamber 150. The internal surface 152 of the piston 142 may also define a distal conduit 160 extending from the septum 156 to a distal aperture 162. The septum 156 may be configured to block fluid communication between the distal aperture 162 and the proximal aperture 158 via the piston 142.

The piston 142 may also include a piston connector 164 disposed on a distal end of the piston 142. The piston connector 164 may be a threaded connector, a tapered connector, an interference connector, a Luer-type connector, or any other connector known in the art. According to an aspect of the disclosure, the piston connector 164 is complementary to the stem connector 124, such that coupling between the piston connector 164 and the stem connector 124 may fix a spatial relationship between the piston 142 and the inner stem 110 of the barrel 102 along the longitudinal direction 130, the radial direction 134, or combinations thereof. According to another aspect of the disclosure, each of the piston connector 164 and the stem connector 124 are aligned with the longitudinal axis 128. According to another aspect of the disclosure, each of the septum 156 and the cannula 126 are aligned with the longitudinal axis 128.

The dose divider 106 includes a flange 170 and a concave shell 172 disposed on the flange 170. The flange 170 of the dose divider 106 extends at least partly in the radial direction 134 beyond a radial extent of the concave shell 172. The concave shell 172 extends at least partly in the longitudinal direction 130 from a distal surface 174 of the flange 170 to a distal surface 176 of the concave shell 172. The dose divider 106 is configured to be removably coupled to a proximal end 178 of the vial 140, such that coupling between the dose divider 106 and the vial 140 may fix a spatial relationship between the dose divider 106 and the vial 140 in the radial direction 134, the longitudinal direction 130, or combinations thereof.

According to an aspect of the disclosure, the dose divider 106 is free from any threaded connections with the plunger 104, and free from any ratcheting mechanisms in cooperation with the plunger 104. According to another aspect of the disclosure, the syringe 100 does not include any spring or resilient member disposed between the dose divider 106 and the plunger 104, which acts to bias a position of the dose divider 106 relative to the plunger 104.

Figure 3A:
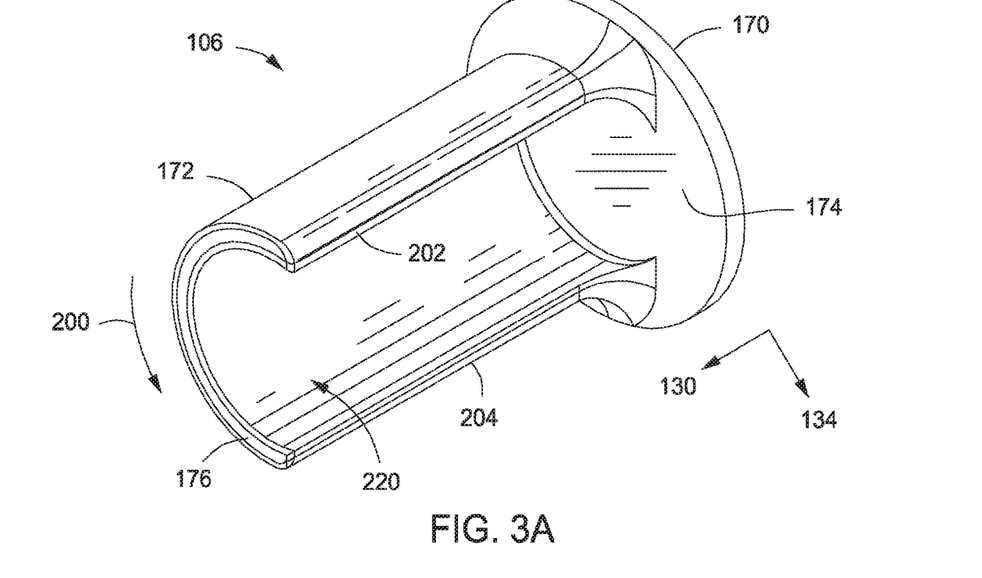
FIG. 3A shows a perspective view of a dose divider, according to an aspect of the disclosure.
Figure 3B:
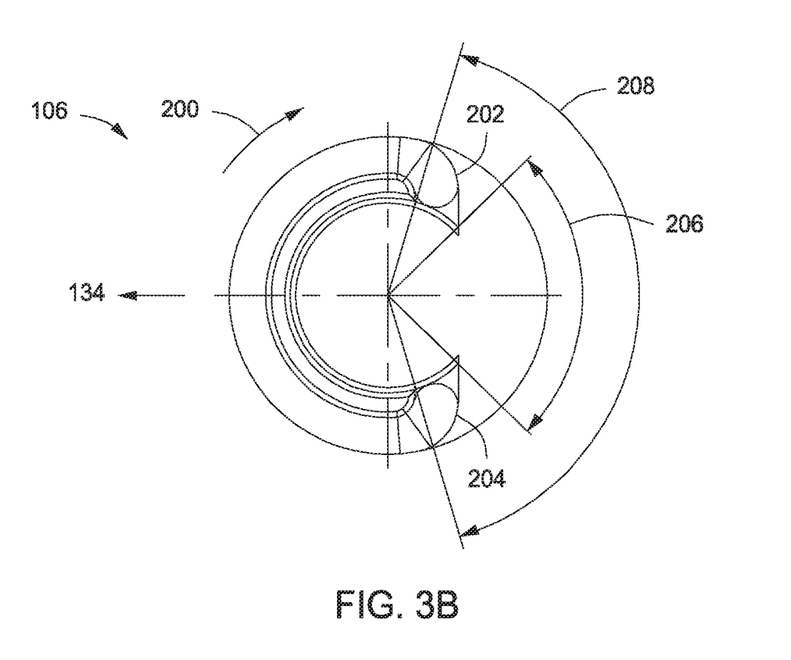
FIG. 3B shows a left side view of a dose divider, according to an aspect of the disclosure.
Figure 3C:
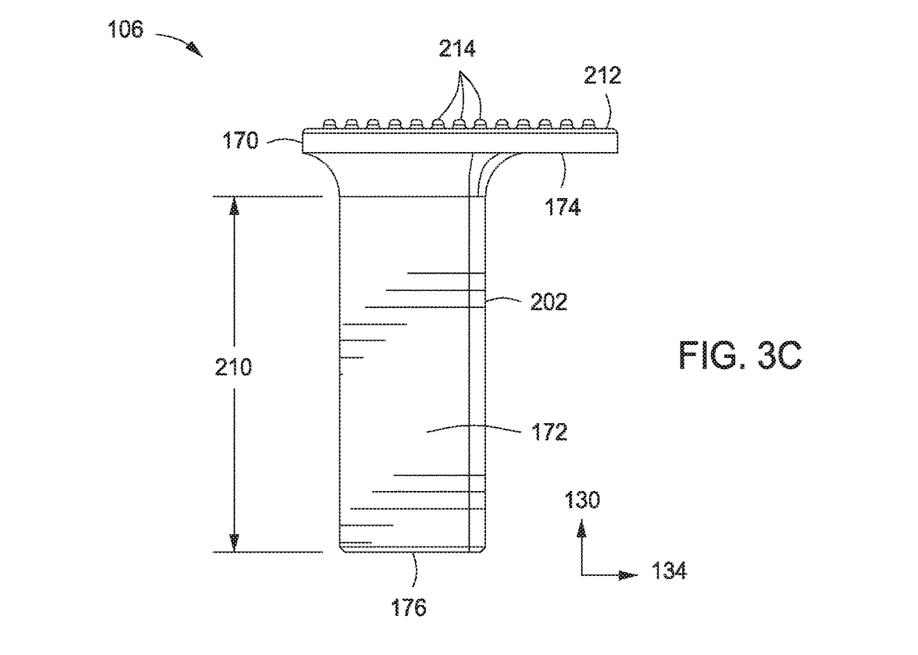
FIG. 3C shows a front view of a dose divider, according to an aspect of the disclosure.
Figure 3D:
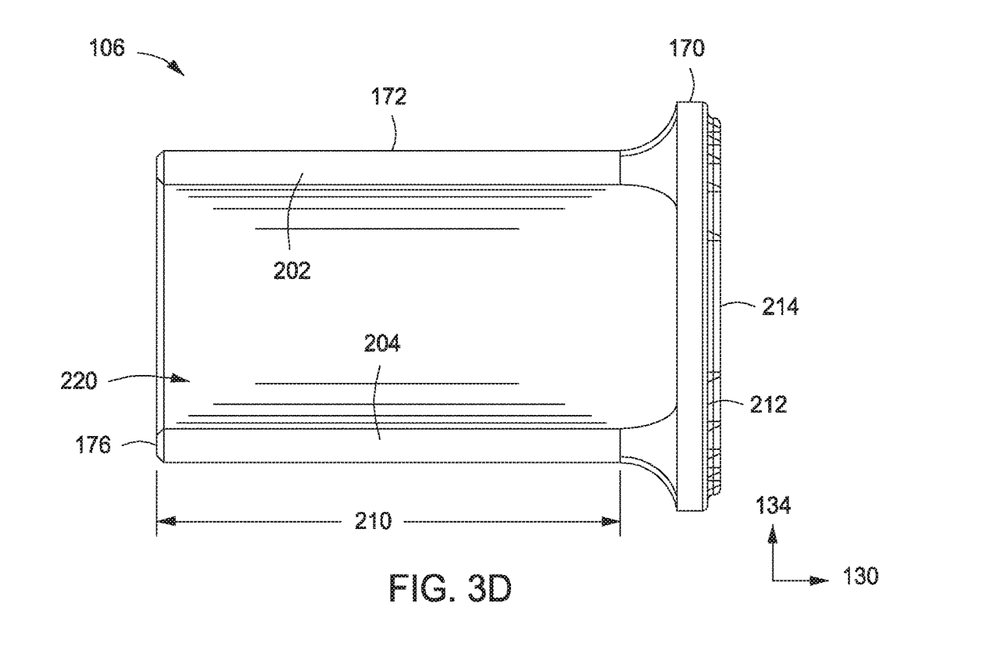
FIG. 3D shows a bottom view of a dose divider, according to an aspect of the disclosure.

Referring to FIGS. 3A, 3B, 3C, and 3D (collectively "FIG. 3"), it will be appreciated that FIG. 3A shows a perspective view of a dose divider 106, according to an aspect of the disclosure; FIG. 3B shows a left side view of a dose divider 106, according to an aspect of the disclosure; FIG. 3C shows a front side view of a dose divider 106, according to an aspect of the disclosure; and FIG. 3D shows a bottom side view of a dose divider 106, according to an aspect of the disclosure. In FIG. 3A, the concave shell 172 extends about a circumferential direction 200 from a first circumferential edge 202 to a second circumferential edge 204, defining a gap therebetween. Accordingly, a concavity 220 of the concave shell 172 may be open to an environment of the dose divider 106 in the radial direction 134 as well as the longitudinal direction 130.

The concave shell 172 may have a generalized cylindrical cross section in a plane defined by the radial direction 134 and the circumferential direction 200. The generalized cylindrical cross section may be a circular cylindrical cross section, a polynomial cylindrical cross section, a square cylindrical cross section, an irregular cylindrical cross section, combinations thereof, or any other cross section known in the art that is configured to effect removable attachment between the dose divider 106 and the plunger 104.

According to an aspect of the disclosure, the dose divider 106 is free to slide along the plunger 104 in the longitudinal direction 130 but fixed with respect to the plunger 104 in the circumferential direction 200. According to another aspect of the disclosure, the dose divider is free to slide along the plunger 104 in both the longitudinal direction 130 and the circumferential direction 200.

A separation between the first circumferential edge 202 and the second circumferential edge 204 may vary along the longitudinal direction 130 from a first circumferential separation angle 206 to a second circumferential separation angle 208. According to an aspect of the disclosure, the first circumferential separation angle 206 is located closer to the flange 170 than the second circumferential separation angle 208 along the longitudinal direction 130, and the second circumferential separation angle 208 is greater than the first circumferential separation angle. According to an aspect of the disclosure, the second circumferential separation angle may be substantially constant along a longitudinal length 210 of the concave shell 172.

According to an aspect of the disclosure, the second circumferential separation angle 208 is less than or equal to 180 degrees. According to another aspect of the disclosure, the second circumferential separation angle 208 is less than or equal to about 170 degrees. According to another aspect of the disclosure, the second circumferential separation angle 208 is less than or equal to 180 degrees and greater than or equal to 90 degrees.

A proximal end 212 of the flange 170 may include texturing features 214 to resist sliding of an operator's finger across the proximal end 212 of the flange 170 along the radial direction 134, the circumferential direction 200, or combinations thereof. The texturing features 214 may include ridges, bumps, knurling, combinations thereof, or any other surface texturing features known in the art.

Figure 4A:
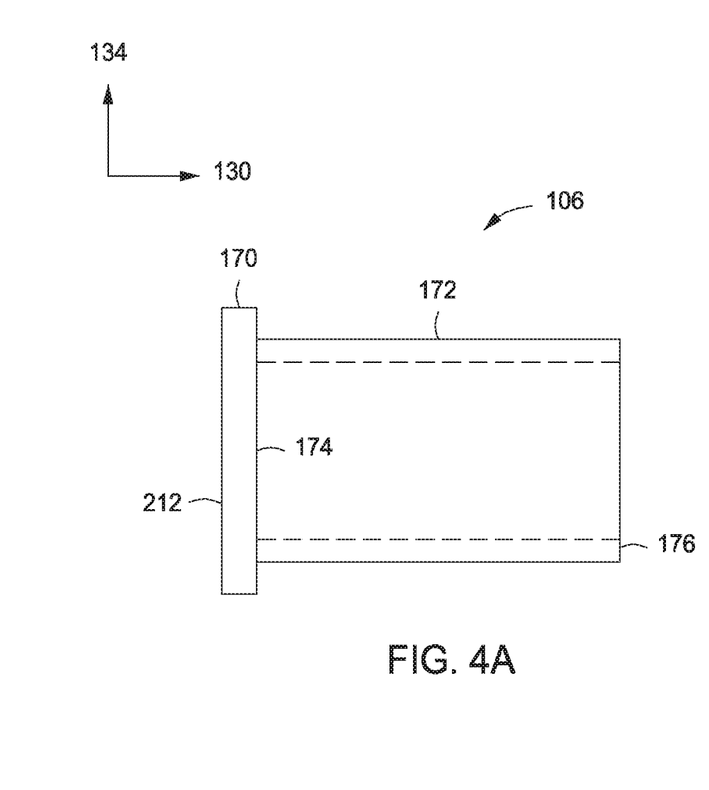
FIG. 4A shows a front view of a dose divider, according to an aspect of the disclosure.
Figure 4B:
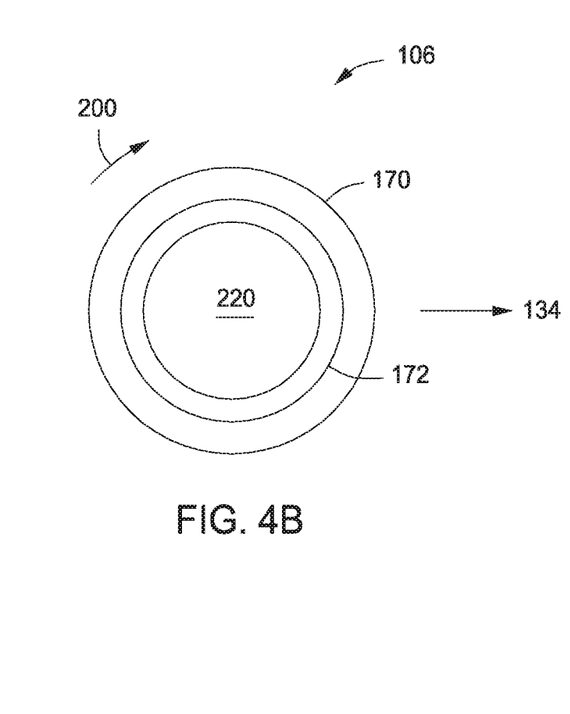
FIG. 4B shows a right side view of a dose divider, according to an aspect of the disclosure.

Referring to FIGS. 4A and 4B (collectively "FIG. 4"), it will be appreciated that FIG. 4A shows a front view of a dose divider 106, according to an aspect of the disclosure; and FIG. 4B shows a right side view of a dose divider 106, according to an aspect of the disclosure. In FIG. 4, the concave shell 172 extends all the way around the dose divider 106 along the circumferential direction 200 over at least part of the length of the concave shell 172 along the longitudinal direction 130. Thus, the concave shell 172 may not include a first circumferential edge 202 and a second circumferential edge 204, as shown in FIG. 3. Further, a concavity 220 of the concave shell 172 may be open to an environment of the dose divider 106 only along the longitudinal direction 130, and not the radial direction 134.

Figure 9A:
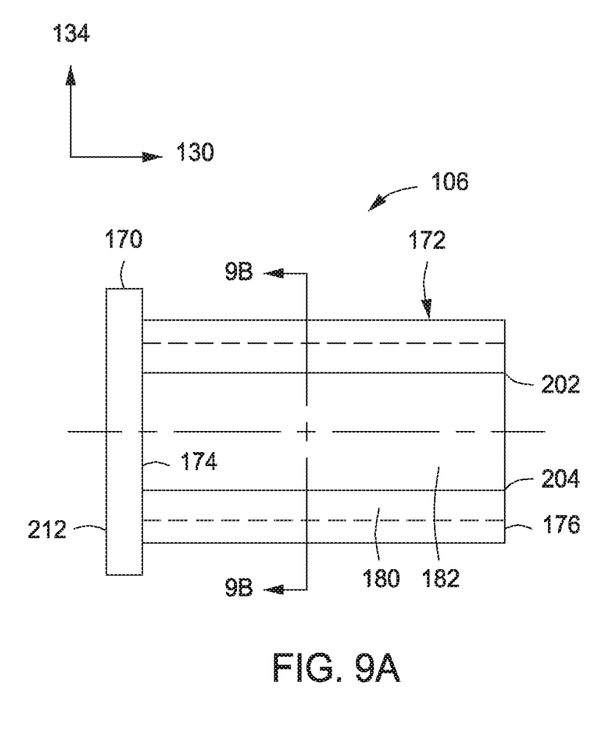
FIG. 9A shows a front view of a dose divider, according to an aspect of the disclosure.
Figure 9B:
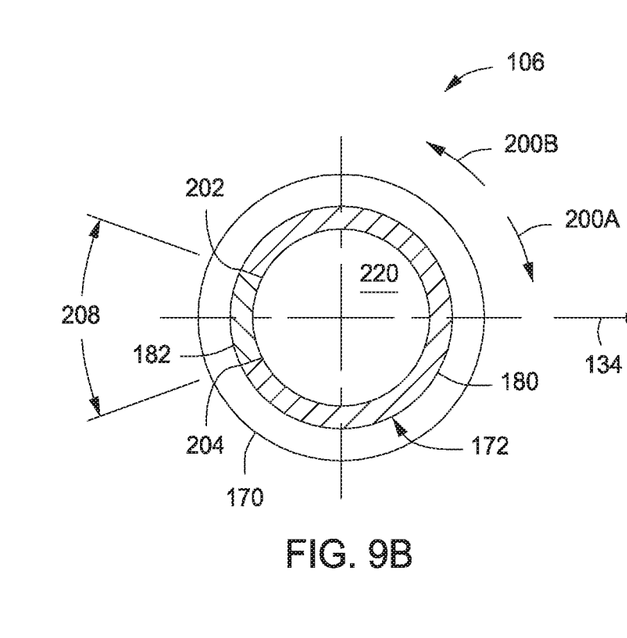
FIG. 9B shows a right side cross sectional view of a dose divider, according to an aspect of the disclosure.

Referring now to FIGS. 9A and 9B (collectively "FIG. 9"), it will be appreciated that FIG. 9A shows a front view of a dose divider 106, according to an aspect of the disclosure; and FIG. 9B shows a right side cross sectional view of a dose divider 106 along section line 9B-9B, according to an aspect of the disclosure. In FIG. 9, the concave shell 172 includes a first portion 180 and a second portion 182. The first portion 180 extends from the first circumferential edge 202 to the second circumferential edge 204 in a clockwise circumferential direction 200A, and the second portion 182 extends from the first circumferential edge 202 to the second circumferential edge 204 in a counterclockwise circumferential direction 200B.

According to an aspect of the disclosure, the first portion 180 includes a first material and the second portion 182 includes a second material, where the first material is different from the second material. According to another aspect of the disclosure, the first portion 180 consists of the first material and the second portion 182 consists of the second material.

Accordingly, it will be appreciated that the first circumferential edge 202 and the second circumferential edge 204 may each be defined by the junction of the first portion 180 and the second portion 182 of the concave shell 172. Further, the circumferential extent of the second portion 182 of the concave shell 172 may subtend the second circumferential separation angle 208, similar to the gap previously discussed with respect to FIG. 3.

The dose divider 106 may be fabricated from a polymer, glass, a ceramic, a metal, wood, combinations thereof, or any other similar material known in the art. According to an aspect of the disclosure, the dose divider 106 includes a polymer that is substantially opaque, such that writing on the plunger 104 is not legible through the dose divider 106. According to another aspect of the disclosure, the dose divider 106 includes a polymer that is substantially transparent or translucent, such that writing on the plunger 104 is legible through the dose divider 106.

Referring now to FIG. 9, the first material of the first portion 180 of the concave shell 172 may have an opacity that is different from an opacity of the second material of the second portion 182. According to an aspect of the disclosure, the first material is substantially opaque and the second material is substantially transparent or translucent. According to another aspect of the disclosure, both the first portion 180 and the second portion 182 of the concave shell 172 are fabricated from a polymer.

Operation of the syringe 100 will now be described with reference to FIGS. 5-8.

Figure 5:
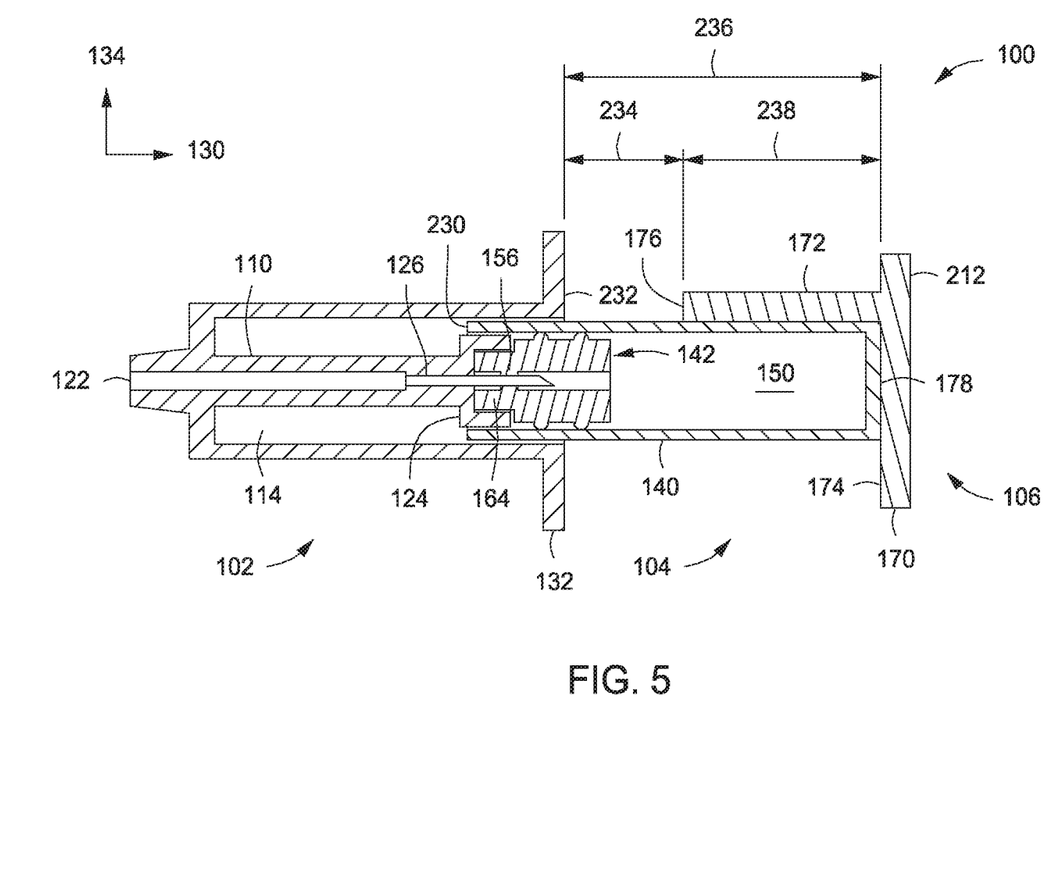
FIG. 5 shows a front cross sectional view of a syringe arranged in a first configuration, according to an aspect of the disclosure.

FIG. 5 shows a front cross sectional view of a syringe 100 arranged in a first configuration, according to an aspect of the disclosure. In FIG. 5, the piston connector 164 is coupled with the stem connector 124, such that the cannula 126 pierces through the septum 156 of the piston 142. In turn, the fluid chamber 150 is in fluid communication with the distal aperture 122 of the stem connector 124 via the cannula 126. A distal end 230 of the vial 140 may be disposed within the barrel cavity 114 when the piston connector 164 is coupled with the stem connector 124.

Referring still to FIG. 5, the dose divider 106 is removably attached to the plunger 104 such that the distal surface 174 of the flange 170 of the dose divider 106 bears on the proximal end 178 of the vial 140. It will be appreciated that the distal surface 174 of the flange 170 may bear on the proximal end 178 of the vial 140 via intermediate structures disposed therebetween, such that the distal surface 174 of the flange 170 does not directly contact the proximal end 178 of the vial 140. According to an aspect of the disclosure, the distal surface 174 of the flange 170 bears on the proximal end 178 of the vial 140 in direct contact.

The concave shell 172 of the dose divider 106 faces at least a portion of the vial 140 along the radial direction 134, the circumferential direction 200, or combinations thereof. In the first configuration, the distal surface 176 of the dose divider 106 is separated from a proximal surface 232 of the flange 132 by a distance 234 along the longitudinal direction 130. According to an aspect of the disclosure, a distance 236 from the proximal end 178 of the vial 140 to the proximal surface 232 of the flange 132, along the longitudinal direction, is equal to the sum of the distance 234 and a distance 238 from the distal surface 174 of the flange 170 to the distal surface 176 of the concave shell 172.

According to another aspect of the disclosure, the distal surface 176 of the dose divider 106 faces the flange 132 of the barrel 102, such that translation of the dose divider 106 toward the flange 132 may result in the distal surface 176 of the dose divider 106 bearing on the flange 132. It will be appreciated that the distal surface 176 of the dose divider 106 may bear on the barrel 102 through intervening components that may transmit a force from the dose divider 106 onto the barrel 102 along the longitudinal direction 130. According to another aspect of the disclosure, the syringe 100 is free from any intervening components between the distal surface 176 of the dose divider 106 and the flange 132 along an projection of the distal surface 176 of the dose divider 106 along the longitudinal direction 130, such that translation of the dose divider 106 toward the barrel 102 may result in the distal surface 176 of the dose divider bearing on the flange 132 in direct contact therebetween.

Translation of the piston 142 toward the proximal end 178 of the vial 140 along the longitudinal direction 130 acts to decrease the volume within the fluid chamber 150, and therefore acts to expel material out of the fluid chamber 150 via the cannula 126 and the distal aperture 122 of the inner stem 110. The piston 142 may be translated toward the proximal end 178 of the vial 140 by translating the vial 140 toward the distal aperture 122 of the inner stem 110 by applying a force on the proximal end 212 of the dose divider 106 along the longitudinal direction 130 toward the distal aperture 122 of the inner stem 110.

According to an aspect of the disclosure, the fluid chamber 150 of the vial 140 is prefilled with a fluid material before the piston connector 164 is coupled with the stem connector 124. According to another aspect of the disclosure, the prefilled material is a medication. However, it will be appreciated that the fluid chamber 150 of the vial 140 may be prefilled with any fluid to suit a particular application of the syringe 100.

Figure 6:
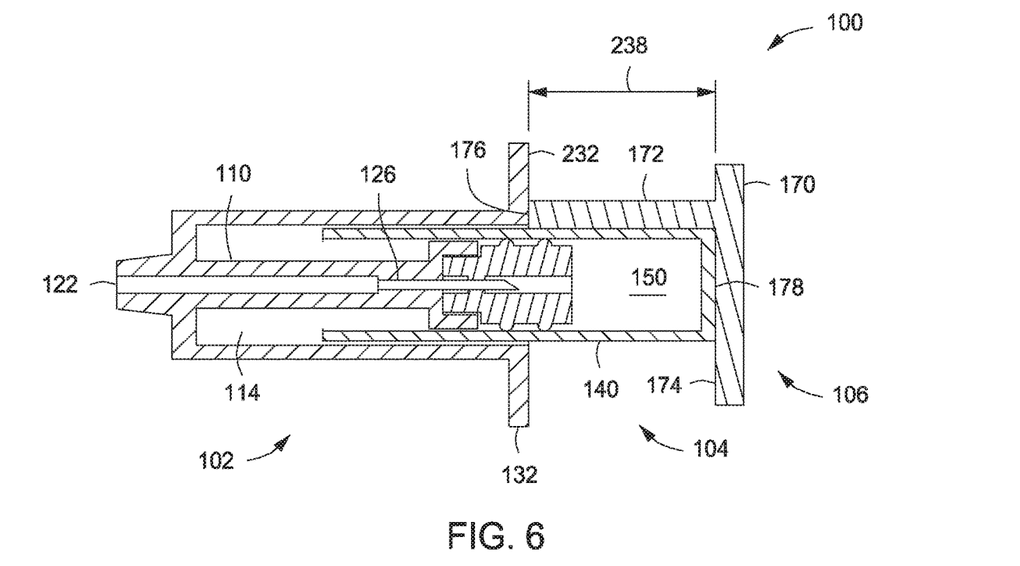
FIG. 6 shows a front cross sectional view of a syringe arranged in a second configuration, according to an aspect of the disclosure.

FIG. 6 shows a front cross sectional view of a syringe 100 arranged in a second configuration, according to an aspect of the disclosure. Similar to the first configuration of the syringe 100 in FIG. 5, the second configuration of the syringe 100 in FIG. 6 has the piston connector 164 coupled with the stem connector 124, such that the cannula 126 pierces through the septum 156 of the piston 142, and the distal surface 174 of the flange 170 of the dose divider 106 bears on the proximal end 178 of the vial 140. However, in the second configuration illustrated in FIG. 6, the vial 140 has been translated toward the distal aperture 122 of the inner stem 110, by the distance 234 (see FIG. 5) for example, such that the distal surface 176 of the concave shell 172 of the dose divider 106 bears on the barrel 102. Thus, between the first configuration (see FIG. 5) and the second configuration of the syringe 100, a first portion of the material contained within the fluid chamber 150 is delivered out of the syringe 100 via the distal aperture 122 of the inner stem 110.

According to an aspect of the disclosure, the distal surface 176 of the concave shell 172 bears on the proximal surface 232 of the flange 132 of the barrel 102 when the syringe 100 is arranged in its second configuration. According to another aspect of the disclosure, the proximal end 178 of the vial 140 may be spaced apart from the proximal surface 232 of the flange 132 by the distance 238, when the syringe 100 is in its second configuration.

Figure 7:
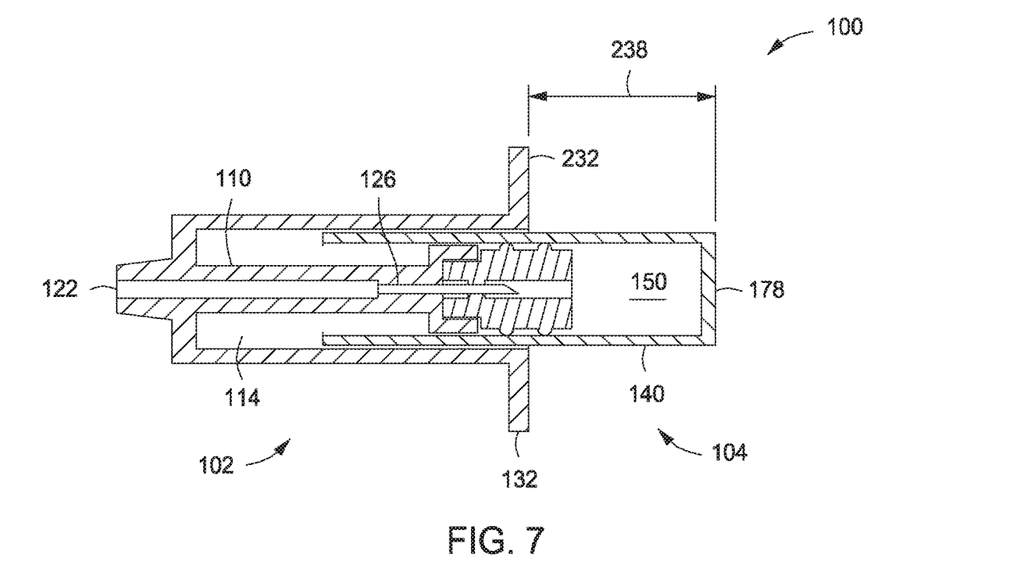
FIG. 7 shows a front cross sectional view of a syringe arranged in a third configuration, according to an aspect of the disclosure.

FIG. 7 shows a front cross sectional view of a syringe 100 arranged in a third configuration, according to an aspect of the disclosure. The vial 140 is in the same, or substantially the same, location relative to the barrel 102 as the second configuration illustrated in FIG. 6; however, in FIG. 7 the dose divider 106 has been removed from the plunger 104. The dose divider 106 may have been removed from the plunger 104 by translating the dose divider 106 relative to the plunger 104 along the longitudinal direction 130, the radial direction 134, or combinations thereof. According to an aspect of the disclosure, the proximal end 178 of the vial 140 is spaced apart from the proximal surface 232 of the flange 132 by the distance 238, when the syringe is in its third configuration.

Figure 8:
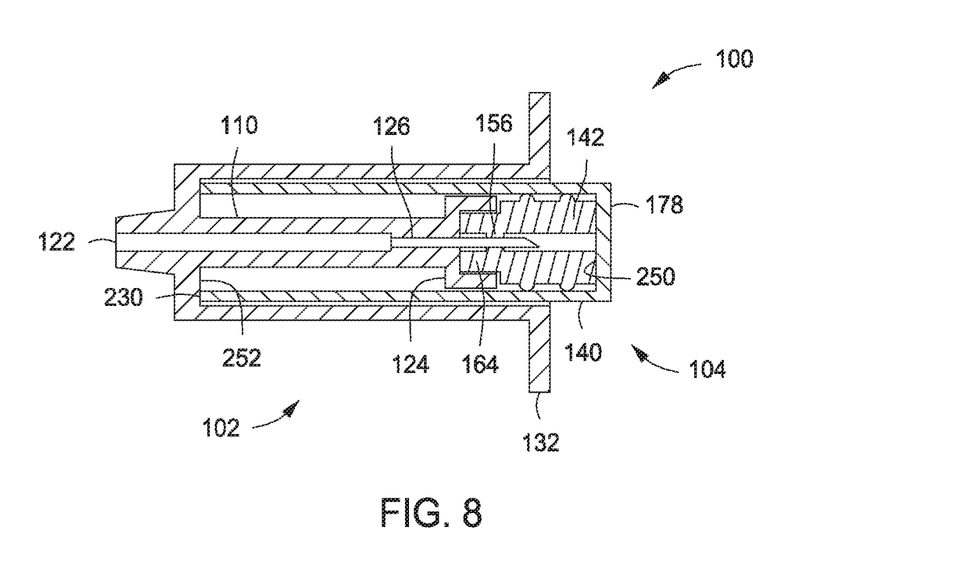
FIG. 8 shows a front cross sectional view of a syringe arranged in a fourth configuration, according to an aspect of the disclosure.

FIG. 8 shows a front cross sectional view of a syringe 100 arranged in a fourth configuration, according to an aspect of the disclosure. Similar to the third configuration of the syringe 100 in FIG. 7, the fourth configuration of the syringe 100 in FIG. 6 has the piston connector 164 coupled with the stem connector 124, such that the cannula 126 pierces through the septum 156 of the piston 142. However, in the fourth configuration illustrated in FIG. 8, the vial 140 has been further translated toward the distal aperture 122 of the inner stem 110 along the longitudinal direction 130, such that a proximal surface 250 of the internal surface 144 of the vial 140 bears on the piston 142, the distal end 230 of the vial 140 bears on a distal surface 252 of the internal surface 112 of the barrel 102, or combinations thereof. Thus, between the third configuration (see FIG. 7) and the fourth configuration of the syringe 100, a second portion of the material contained within the fluid chamber 150 (see FIG. 7) is delivered out of the syringe 100 via the distal aperture 122 of the inner stem 110. According to an aspect of the disclosure, a quantity of the second portion of material delivered by the syringe 100 is substantially equal to a quantity of the first portion of material delivered by the syringe 100.

The present disclosure is applicable to syringes in general, and more particularly, to syringes that provide tactile feedback to the user of material quantity delivered from the syringes. Further, the present disclosure may be applicable to syringes used in the context of medicine, manufacturing, construction, maintenance and repair, agriculture, food preparation, or any other context where syringes may be used. Accordingly, aspects of the disclosure may be applied to syringes for delivering a medication to a patient, or delivering other fluid materials such as air, adhesives, lubricants, food products, and the like.

Applicants have identified a need for delivering multiple doses of medication from a single syringe using rapid plunger motion to deliver each of the multiple doses. For example, nasal administration of medications may benefit from delivery of partial doses to each nostril of a patient in quick succession and with a high degree of atomization.

The degree of atomization increases with increasing pressure drop across the atomization orifice, and therefore, increasing flow rate through the atomization orifice. Accordingly, the degree of atomization may benefit from higher velocities of the plunger 104 relative to the barrel 102 during medicine delivery. In turn, Applicants have discovered that high plunger velocities for multi-dose syringes may result in repeatability and reproducibility errors, in both the amount of medicine in each dose and the degree of atomization, when dose quantity is controlled via visual feedback of a relative position of the plunger 104 within the barrel 102 of the syringe 100. Indeed, errors in dose quantity based on visual feedback may be exacerbated by the need for high plunger velocities at least because of difficulty in rapidly decelerating the plunger 104 while simultaneously stopping precisely at the longitudinal location corresponding to a desired dose.

Aspects of the disclosure address drawbacks of conventional approaches by providing tactile dose feedback through variable interference between the dose divider 106 and the barrel 102 of a syringe 100, using an economical and intuitive structure. As described previously, the dose divider 106 is removably coupled to the plunger 104 to provide variable degrees of tactile interference between the dose divider 106 and the barrel 102. Indeed, by providing variable degrees of interference between the dose divider 106 and the barrel 102 to limit the individual dose quantities, syringe users may allocate more attention to the rate of plunger travel and the location of the distal aperture 122 of the syringe 100 relative to a patient's nose, thereby improving repeatability and reproducibility of both dose quantity and the degree of atomization.

Further, aspects of the disclosure provide a syringe kit, including a barrel 102, a pre-filled vial 140, and a dose divider 106, where a user assembles the kit to construct a syringe 100 according to aspects of the disclosure.

The syringe 100 may be configured such that the first portion of material delivered from the syringe 100 may be substantially equal in quantity to the second portion of material delivered from the syringe 100. However, it will be appreciated that the syringe 100 may also be configured such that the quantity of the first portion of material is different from the quantity of the second portion of material for other material delivery processes.

Unless specified otherwise herein, the word "substantially" shall mean "considerable in extent," or shall mean "largely but not necessarily wholly that which is specified."

It will be appreciated that the foregoing description provides examples of the disclosed apparatus and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The invention claimed is:

1. A syringe, comprising:
    a barrel having an internal surface defining an internal bore therein, a distal end of the barrel defining an outlet port;
    a plunger having a distal end disposed within the internal bore of the barrel, and a proximal end disposed outside the internal bore of the barrel, the proximal end of the plunger being opposite the distal end of the plunger along a longitudinal direction, the plunger including a vial having an internal volume, the internal volume being in fluid communication with the outlet port of the barrel; and a dose divider removably coupled to the plunger, the dose divider is configured, upon application of a force to the dose divider, to translate the plunger a predetermined distance along the longitudinal direction and to bear on the barrel to stop translation of the plunger beyond the predetermined distance, the dose divider comprising:

a flange extending at least partly in a radial direction, the flange having a distal surface that faces the barrel and that also faces and bears upon the proximal end of the plunger; and a concave shell extending away from the flange along the longitudinal direction, the longitudinal direction being perpendicular to the radial direction, a proximal end of the concave shell being disposed on the flange, and a distal end of the concave shell being opposite the proximal end of the concave shell along the longitudinal direction, the concave shell extending in a circumferential direction about an axis from a first circumferential edge to a second circumferential edge, the axis being aligned with the longitudinal direction, the first circumferential edge being separated from the second circumferential edge by a gap distance, and the concave shell of the dose divider extending away from the distal surface of the flange of the dose divider along the longitudinal direction, a length of the dose divider in said longitudinal direction being shorter than a length of the plunger, wherein the first circumferential edge and the second circumferential edge extend linearly in the longitudinal direction from the proximal end of the concave shell to the distal end of the concave shell the concave shell of the dose divider subtends an angle in the circumferential direction about the axis from the first circumferential edge to the second circumferential edge that is greater than 180 degrees, and the concave shell of the dose divider further includes a concavity open to an environment of the dose divider in the radial direction as well as the longitudinal direction.

2. The syringe as claimed in claim 1, wherein the gap distance of the dose divider spans a first distance at the proximal end of the concave shell, the gap distance spans a second distance at the distal end of the concave shell, and the second distance is greater than the first distance.

3. The syringe as claimed in claim 1, wherein the angle in the circumferential direction is less than 270 degrees.

4. The syringe as claimed in claim 1, wherein the angle in the circumferential direction is less than 230 degrees.

5. The syringe as claimed in claim 1, wherein
the barrel includes a flange and a distal surface of the concave shell of the dose divider faces the flange of the barrel, such that translation of the dose divider toward the flange of the barrel over a prescribed distance results in the distal surface of the concave shell bearing on the flange of the barrel.

6. A method for delivering a material using a syringe as claimed in claim 1, comprising:

installing the dose divider on the proximal end of the plunger, such that the concave shell of the dose divider at least partly surrounds the plunger about a longitudinal axis of the plunger;

expelling a first portion of the material from the syringe by translating the plunger from a first position to a second position relative to the barrel along the longitudinal axis;

bearing the distal end of the concave shell of the dose divider against the barrel;

removing the dose divider from the plunger; and expelling a second portion of the material from the syringe by translating the plunger from the second position to a third position relative to the barrel along the longitudinal axis.

7. The method as claimed in claim 6, wherein the vial is a removable vial, and the internal volume of the plunger includes the internal volume of the removable vial.

8. The method as claimed in claim 6, wherein the gap distance of the dose divider spans a first distance at the proximal end of the concave shell, the gap distance spans a second distance at the distal end of the concave shell, and the second distance is greater than the first distance.

9. The method as claimed in claim 6, wherein the angle in the circumferential direction is less than 270 degrees.

10. The method as claimed in claim 9, wherein the angle in the circumferential direction is less than 230 degrees.

11. The syringe as claimed in claim 1, wherein the distal surface of the flange of the dose divider bears upon a surface of the proximal end of the plunger that faces away from the barrel in the longitudinal direction.

12. The syringe as claimed in claim 1, wherein the distal end of the concave shell includes a planar distal surface at a distal-most portion of the concave shell, the planar distal surface provided continuously in a plane that extends in the radial direction and in a direction perpendicular to the radial direction, the plane being perpendicular to the longitudinal direction.

* * * * *